(12) United States Patent
Stone

(10) Patent No.: US 6,443,908 B2
(45) Date of Patent: Sep. 3, 2002

(54) METHOD AND APPARATUS FOR IN VIVO MEASUREMENT OF CARBON MONOXIDE PRODUCTION RATE

(75) Inventor: Robert T. Stone, Sunnyvale, CA (US)

(73) Assignee: Kinderlife Instruments, Inc., Mountain View, CA (US)

(*) Notice: Subject to any disclaimer, the term of this patent is extended or adjusted under 35 U.S.C. 154(b) by 0 days.

(21) Appl. No.: 09/803,237

(22) Filed: Mar. 8, 2001

Related U.S. Application Data
(60) Provisional application No. 60/189,002, filed on Mar. 13, 2000.

(51) Int. Cl.[7] ............................................. A61B 5/08
(52) U.S. Cl. ..................................................... 600/532
(58) Field of Search ............................... 600/529, 531, 600/532, 533, 538

(56) References Cited

U.S. PATENT DOCUMENTS

| | | | |
|---|---|---|---|
| 4,831,024 A | | 5/1989 | Vreman et al. |
| 5,022,406 A | * | 6/1991 | Tomlinson ................. 600/532 |
| 5,293,875 A | | 3/1994 | Stone |
| 5,357,971 A | * | 10/1994 | Sheehan et al. ........ 128/205.12 |
| 5,383,469 A | * | 1/1995 | Vreman et al. ............. 600/532 |

* cited by examiner

Primary Examiner—Kevin Shaver
Assistant Examiner—Navin Natnithithadha
(74) Attorney, Agent, or Firm—Francis Law Group

(57) ABSTRACT

An apparatus for in vivo measurement of carbon monoxide production rate comprising a first gas detector for detecting the concentration of a first selected gas in at least first and second gas samples, the first gas detector being adapted to provide output signals corresponding to the first selected gas concentration in the first and second gas samples; a second gas detector adapted to substantially simultaneously detect the concentration of at least second and third selected gases in the first and second gas samples, the second gas detector being further adapted to provide output signals corresponding to the second and third selected gas concentrations in the first and second gas samples; means for providing the first and second gas samples to the first and second gas detectors; and processing means for determining the rate of carbon monoxide production in at least the second sample in response to the first and second gas detectors output signals.

14 Claims, 3 Drawing Sheets

US 6,443,908 B2

METHOD AND APPARATUS FOR IN VIVO MEASUREMENT OF CARBON MONOXIDE PRODUCTION RATE

CROSS REFERENCE TO RELATED APPLICATIONS

This application claims benefit under 35 U.S.C. 119 (e) of U.S. Provisional Application No. 60/189,002, filed Mar. 13, 2000.

FIELD OF THE INVENTION

This invention relates to methods and apparatus for in vivo measurement of carbon monoxide concentration in the exhaled breath of a patient. More particularly, the invention relates to a method and apparatus for direct measurement of the carbon monoxide production rate of a patient.

BACKGROUND OF THE INVENTION

It is known that hemoglobin, myoglobin, and a series of heme enzymes, which reside principally in the liver, are the major hemoproteins. It is also well known that the end products of the catabolism of the heme moiety of these compounds are (1) iron, which is conserved, (2) carbon monoxide (CO), which is normally excreted in the breath, and (3) bilirubin, which is excreted by the liver and chemically modified in the gastrointestinal tract to a series of urobilins.

The principal source of CO and of bilirubin—each a surrogate for the other—is from the catabolism of circulating red cells at the end of their life span. A small portion of CO is also derived from cytoplasmic hemoglobin released as a shroud during enucleation of normoblasts and from aborted red blood cell precursors that never reach the peripheral blood (i.e., ineffective erythropiesis).

The rate of CO excretion (or production) is thus clinically significant. For example, in patents with hemolytic anemias, hematologists need a measure of the effectiveness of therapy. Usually they rely principally on an increase in the hematocrit or a decrease in the reticulocyte count. An increase in hematocrit is comparatively slow, whereas a decrease in reticulocyte count is more rapid.

It is likely that if treatment were effective very rapidly (i.e., instantaneously) it would take 5 to 7 days for the reticulocyte count to decrease to normal levels because of maturing red cell precursors already in the formative-stage pipeline in the bone marrow. Moreover, reticulocyte levels may be altered by intercurrent conditions such as inflammation and infections.

By contrast, the rate of carbon monoxide excretion typically decreases rapidly to normal levels within hours and will more accurately reflect hemolytic rates, as would the plasma unconjugated bilirubin concentration.

Carbon monoxide excretion has two (2) distinct components. The first represents endogeneous production of CO. The second accrues from exogenous CO absorbed from the atmosphere, both in smokers and non-smokers.

Various non-invasive methods (and apparatus) have been employed to determine the concentration of carbon monoxide in the breath. One method includes incrementally acquiring a sample of "end-tidal" breath and analyzing the acquired sample by mass spectroscopy or gas chromatography to determine the end-tidal carbon monoxide concentration. The sample is obtained by extracting from each of several successive breaths a portion of the apparent end-tidal breath using a syringe. The end-tidal portion of breath is determined by observing the chest movements of the infant. See, e.g., Vreman et al., U.S. Pat. No. 4,831,024.

A major drawback with this method is that the results merely provide an estimate of the carbon monoxide concentration, not the rate of carbon monoxide production.

A further problem with this method is that accurate assessment of the concentration difference in carbon monoxide requires obtaining good samples of end-tidal patient breath. This essentially requires that the patient have a regular, predictable breathing cycle. Thus, it can be difficult to obtain a good sample by watching chest wall movement, particularly for a newborn and for patients having irregular breathing cycles.

In U.S. Pat. No. 5,293,875 further methods and apparatus are disclosed for measuring the end-tidal carbon monoxide concentration in a patient's breath. The method comprises measuring the room carbon monoxide concentration, end-tidal carbon dioxide concentration ($ETCO_2$), the average carbon dioxide concentration, and the average carbon monoxide concentration in the patient's breath. From this data, the apparatus computes the end-tidal carbon monoxide "concentration" corrected for room air and the index of $CO/CO_2$.

A major drawback of the '875 method is that the index of $CO/CO_2$ is a derived parameter, which, according to the invention, "may" relate the rate of carbon monoxide production to the degree of hemolysis. The apparatus is thus incapable of providing a direct measure of the carbon monoxide production rate.

Further, the apparatus employs a conventional electrochemical sensor. Such sensors are sensitive to many other gases such as hydrogen ($H_2$), and are therefore susceptible to error.

It is well known that hydrogen is a waste product, emanating from the gastrointestinal system, which is also normally excreted in the breath. The hydrogen typically evolves from various digestive abnormalities, such as lactose intolerance, or the inability to thoroughly digest the carbohydrates and/or disaccharides contained in the system. When this occurs, bacteria will digest the noted substances and give off hydrogen as a bi-product.

Another problem with conventional sensors is that the measurement dynamics of the sample gas transport through the gas permeable membrane and oxidation-reduction in the electrochemical cell results in a relatively slow response time such that discrete samples of the end-tidal breath must be obtained and analyzed to determine the end-tidal carbon monoxide concentration.

It is therefore an object of the present invention to provide an improved method and apparatus for the in vivo measurement of carbon monoxide production rate.

It is another object of the invention to provide a method and apparatus for "direct", rapid, real-time assessment of the level of hemolysis in the blood.

It is yet another object of the invention to provide a method and apparatus for assessment of carbon monoxide production rate that substantially reduces the errors associated with the $H_2$ excretion.

SUMMARY OF THE INVENTION

In accordance with the above objects and those that will be mentioned and will become apparent below, the apparatus for in vivo measurement of carbon monoxide production rate in accordance with this invention comprises a first gas detector for detecting the concentration of a first selected gas in at least first and second gas samples, the first gas detector being adapted to provide output signals corresponding to the first selected gas concentration in the first and second gas samples; a second gas detector adapted to substantially simultaneously detect the concentration of at least second and third selected gases in the first and second gas samples, the second gas detector being further adapted to provide output signals corresponding to the second and third selected gas concentrations in the first and second gas samples; means for providing the first and second gas samples to the first and second gas detectors; and processing means for determining the rate of carbon monoxide production in at least the second sample in response to the first and second gas detectors output signals.

The method of determining the carbon monoxide production rate in a subject in accordance with the invention comprises the steps of (a) introducing a room air sample to first and second gas detectors during a first period of time; (b) detecting the concentration of carbon dioxide in the room air sample ($CO_2$) during the first period of time; (c) substantially simultaneously detecting the concentration of carbon monoxide in the room air sample (CO) and the concentration of hydrogen in the room air sample ($H_2$) during the first period of time; (d) introducing a breath sample from the subject to the first and second gas detectors during a second period of time; (e) measuring the concentration of carbon dioxide in the breath sample ($CO_2'$) during the second period of time; (f) substantially simultaneously measuring the concentration of carbon monoxide in the breath sample (CO') and the concentration of hydrogen in the breath sample ($H_2'$) during the second period of time; (g) comparing the $CO_2'$, CO', and $H_2'$ detected in the breath sample to the $CO_2$, CO and $H_2$ detected in the room air sample to derive corrected carbon dioxide ($CO_2''$), carbon monoxide (CO'') and hydrogen ($H_2''$) values; and (h) determining the carbon monoxide production rate ($\dot{V}CO$) from the following relationship:

$$VCO = \int_{t_1}^{t_0} CO'' dt$$

where:

$t_1 - t_0$ = the second period of time

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DESCRIPTION OF THE PREFERRED EMBODIMENT

The present invention substantially reduces or eliminates the drawbacks and disadvantages associated with prior art carbon monoxide testing methods and apparatus. As discussed in detail below, in contrast to prior art methods and apparatus which merely provide an assessment of the carbon monoxide "concentration" in a patient's breath, the method and apparatus of the invention provides a rapid, in vivo assessment of the carbon monoxide "production rate" in a patient.

As will be appreciated by one having skill in the art, the method and apparatus of the invention may thus be employed in a hospital nursery, clinic, or physician's office to provide a rapid, accurate assessment of the level of hemolysis, which, if abnormally high, could lead to various adverse consequences, such as hyperbilirubinemia and jaundice.

Figure 1:
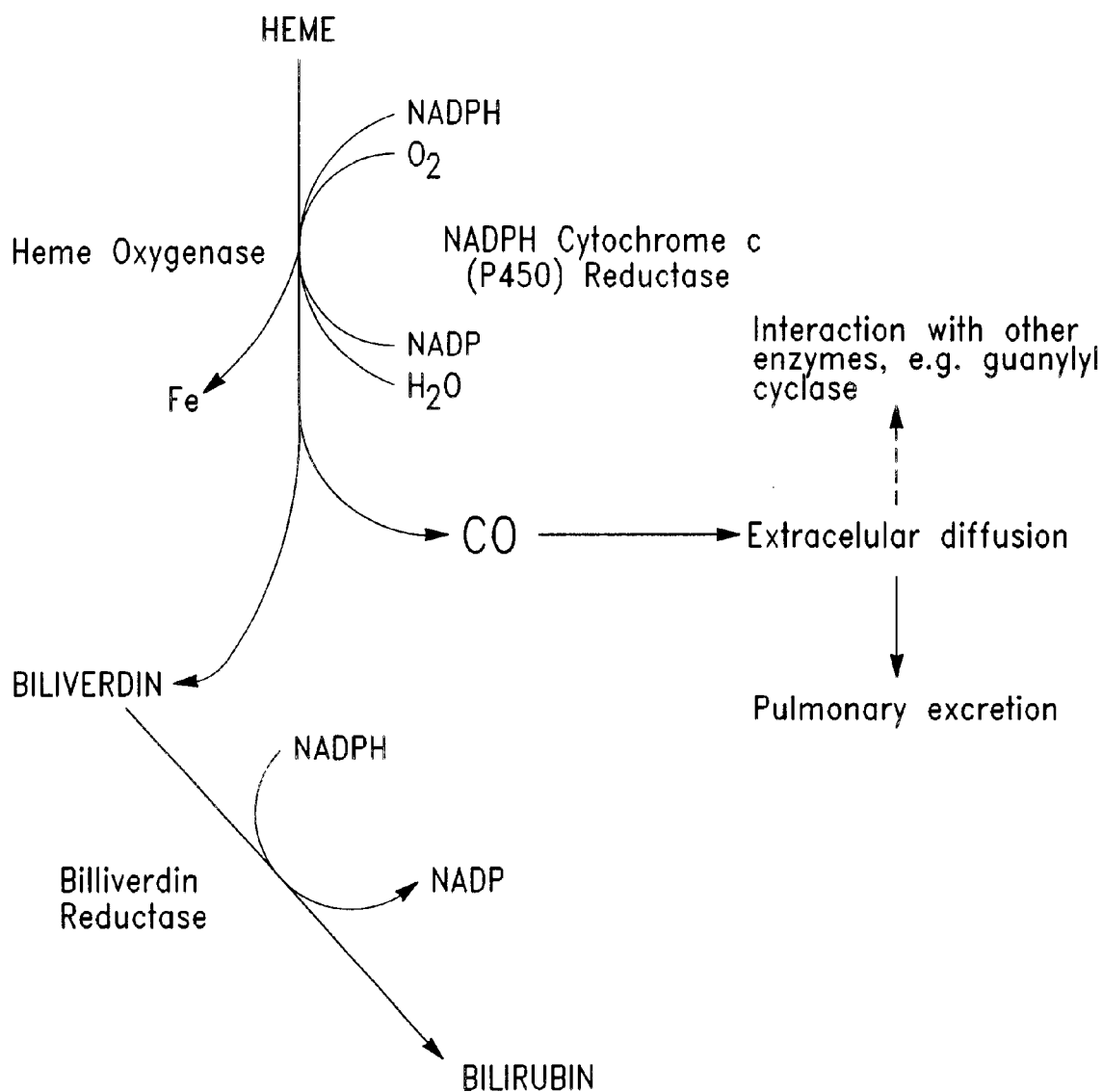
FIG. 1 is a schematic illustration of the heme oxygenase-dependent production of CO.

Referring first to FIG. 1, there is shown an illustration of the heme oxygenase-dependant production of CO. The heme degradation reaction mechanism generating CO and bilirubin is complex and involves the integrated action of three enzymes: microsomal heme oxygenase, microsomal nicotinamide-adenine dinucleotide phosphate (NADPH)-cytochrome c (P-450) reductase, and cytosolic biliverdin reductase.

In the first step of this integrated system, heme is auto-catalyzed at the boundary of the cytosol and the endoplasmic reticulum. Ferric (Fe(III)) heme typically binds to heme oxygenase in a 1:1 molar ratio. Heme is reduced to the ferrous (Fe(II)) state by the transfer of reducing equivalents through interaction with NADPH-cytochrome c (P-450) reductase. In the ferrous state, heme binds molecular oxygen ($O_2$) and is altered through a sequence of steps involving several intermediates, leading to autooxidation.

With reduction of the alpha-hydroxyheme intermediate, the alpha methene bridge carbon is eliminated as CO. The Fe(II) component is released from the enzyme complex during the final step in the HO reaction mechanism, and generated biliverdin is subsequently reduced to bilirubin by the cytosolic enzyme, biliverdin reductase.

The complete heme degradation reaction with its microsomal and cytosolic components results in the equimolar formation of CO and bilirubin per mole of heme degraded. Because of this relationship, in-vitro and in vivo measurements of CO have been used both as an index of heme catabolism and bilirubin production. However, as discussed above, the CO measured by conventional methods and apparatus is typically limited to CO "concentration", not the clinically significant CO "production rate."

Figure 2:
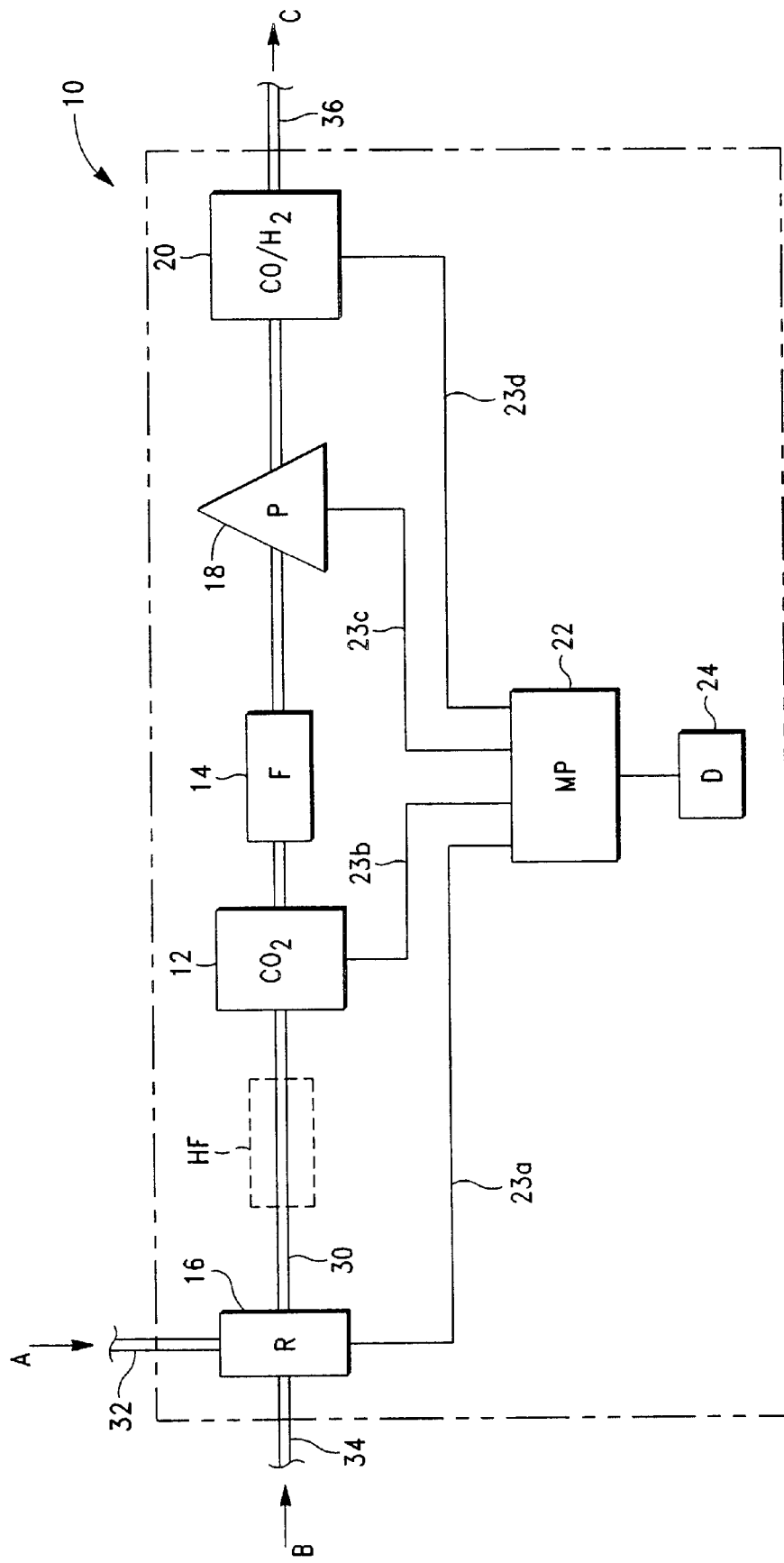
FIG. 2 is a schematic illustration of one embodiment of the apparatus for in vivo measurement of carbon monoxide production rate according to the invention.

Referring now to FIG. 2, there is shown a preferred embodiment of the method and apparatus of the invention.

The apparatus 10 includes a carbon dioxide ($CO_2$) detector 12, an organic vapor filter 14, a flow regulator 16, a pump 18, a combined carbon monoxide/hydrogen ($CO/H_2$) detector 20, and a microprocessor 22.

As illustrated in FIG. 2, the $CO_2$ detector 12, organic filter 14, flow regulator 16, pump 18 and $CO/H_2$ detector 20 are in fluid communication via flow line or tubing 30. The $CO_2$ detector 12, flow regulator 16, pump 18 and $CO/H_2$ detector 20 are also in communication with the microprocessor 22 via lines 23a–23d.

In additional envisioned embodiments of the invention, the apparatus 10 includes a hydrophobic filter (shown in phantom and denoted HF) disposed between the flow regulator 16 and $CO_2$ detector 12 and in communication therewith via flow line 30. As will be appreciated by one having ordinary skill in the art, the hydrophobic filter (HF) would substantially reduce or eliminate any moisture in the gas or flow line 30 (e.g., condensate) which could interfere with the detection of carbon dioxide ($CO_2$).

The $CO_2$ detector 12 is employed to provide at least a first signal corresponding to the sensed concentration of carbon dioxide in the standard (i.e., room air) and at least a second signal corresponding to the sensed concentration of carbon dioxide in the analyte stream (or sample). As will be appreciated by one having skill in the art, various carbon dioxide gas detectors and/or analyzers may be employed within the scope of the invention, such as the Servomex Model No. 1505 fast-response carbon dioxide infrared transducer.

The organic vapor filter 14, which is preferably disposed between the $CO_2$ detector 12 and the pump 18, contains any medium that will absorb organic vapors and reducing gases that might interfere with detecting carbon monoxide. In a preferred embodiment, filter 14 contains activated charcoal.

As illustrated in FIG. 2, the flow regulator 16 preferably includes two (2) gas input lines; a first "standard" line 32 in communication with the atmosphere (i.e., room air), and a second "sample" line 34 in communication with the sampling chamber 42 (see FIG. 3), discussed in detail below. According to the invention, the flow regulator 16 is disposed proximate the hydrophobic filter 15 and is adapted to selectively direct a gas sample from the atmosphere (i.e., standard), denoted by arrow A, or analyte stream (i.e., breath sample) from the chamber 42, denoted by arrow B, to filter 15. The flow regulator 16 also limits the flow rate of the analyte gas stream and standard.

Disposed proximate the $CO/H_2$ detector 20 is the flow inducing means of the invention. In contrast to prior art methods which assess the concentration of carbon monoxide in the end-tidal portion of the breath and, hence, require a constant flow rate (see, e.g., U.S. Pat. No. 5,293,875), the method of the present invention does not require a constant flow rate of the analyte gas stream. Thus, various flow inducing means may be employed within the scope of the invention, such as a positive displacement pump and a fan/flow sensor assembly.

In the embodiment of the invention shown in FIG. 2, the flow inducing means comprises a positive displacement pump 18. According to the invention, the pump 18 and regulator 16 are adjusted so that flow through line 30 is maintained in the range of approximately 40 to 60 ml/min., more preferably, 45 to 55 ml/min. The pump 18 is also adapted to expel the analyte flow stream out exhaust 36 and into the atmosphere, denoted by arrow C.

A key component of the apparatus is the novel $CO/H_2$ detector 20, which is adapted to substantially simultaneously detect both CO and $H_2$. In a preferred embodiment, the $CO/H_2$ is adapted to provide at least a first plurality of signals $C_1$–$C_N$ proportional to the concentration of CO in the analyte stream and at least a second plurality of signals $C'_1$–$C'_N$ proportional to the concentration of $H_2$ in the sample; the signals $C_1$–$C_N$, $C'_1$–$C'_N$ being provided over a predetermined period of time, i.e., $t_1$ through $t_0$.

Microprocessor 22 is employed to control the operation of the apparatus 10. As illustrated in FIG. 2, the microprocessor 22 is connected to and, hence, in communication with the regulator 16, $CO_2$ detector 12, pump 18 and $CO/H_2$ detector 20 to control the noted components.

The microprocessor 22 is further adapted to receive and respond to the output signals from the $CO_2$ and $CO/H_2$ detectors 12, 20 corresponding to the sensed $CO_2$, CO and $H_2$ concentration. These signals are then processed according to the algorithm discussed below to compute a value corresponding to the rate of CO and $H_2$ production. The computed values may then be displayed on a display device 24, such as a liquid crystal display (LED) device.

According to the invention, the display device 24 is adapted to provide a display corresponding to at least the (i) $CO_2$ concentration ($CCO_2$) in the standard and the analyte stream, (ii) the CO concentration in the standard, (iii) the $H_2$ concentration in the standard, (iv) the rate of CO production ($\dot{V}CO$) in the analyte stream, (v) and the rate of $H_2$ production ($\dot{V}H_2$) in the analyte stream. Preferably, display 24 includes a display screen for alphanumeric text, including the determined $CCO_2$, $\dot{V}CO$ and $\dot{V}H_2$, and instructions to the operator for operating the apparatus 10 to acquire the appropriate gas samples.

In additional envisioned embodiments of the invention, the display device includes a keyboard for operator input. The display device 24 may also include a paper printer or have an associated printer (not shown) for providing a printed copy of the parameters determined and/or measured, in character text or graphic form. Alternately, or in addition, audible sounds, visual indicators or lights may be used to prompt the operator to perform the appropriate act.

Figure 3:
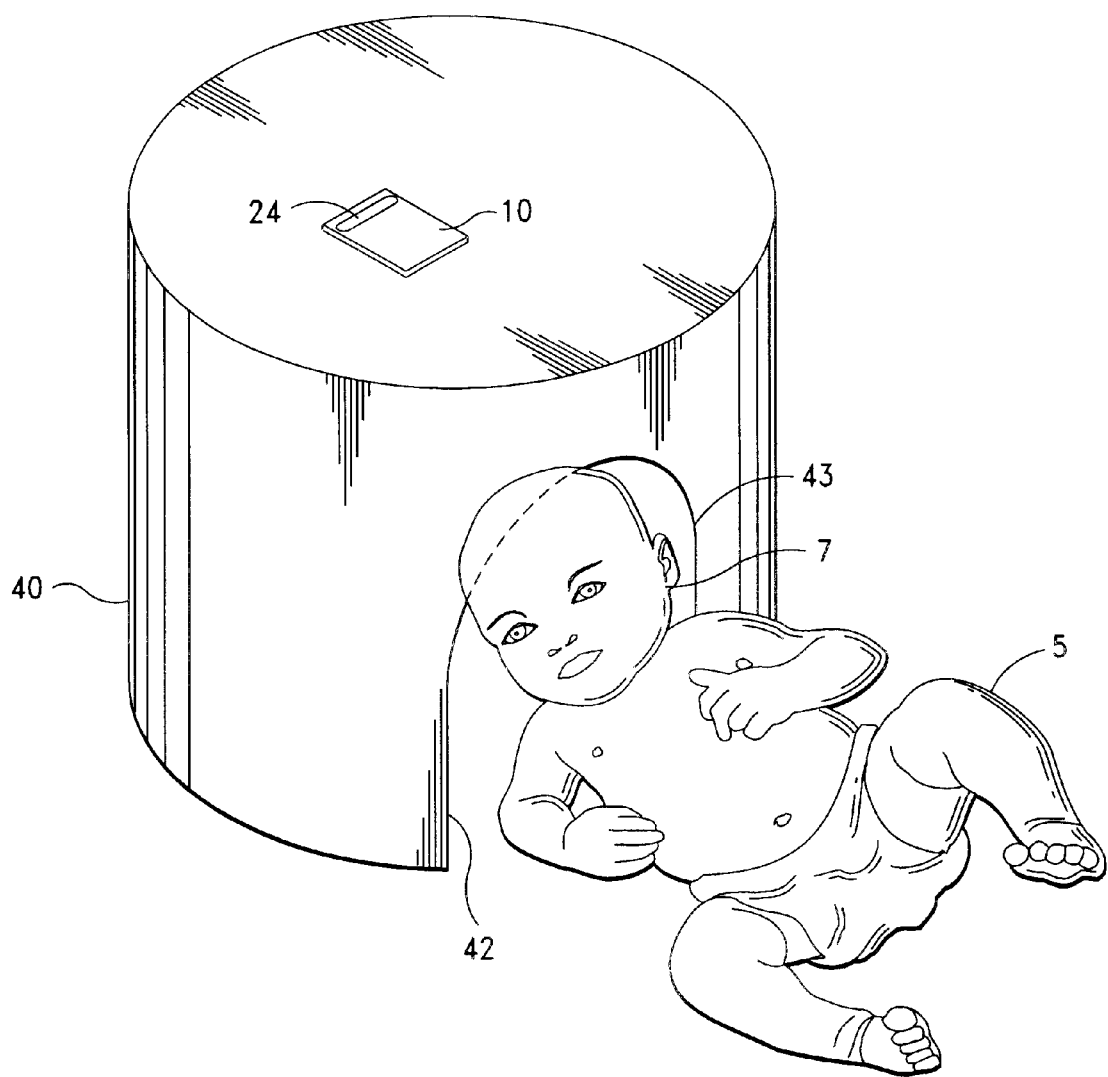
FIG. 3 is an illustration of a test hood incorporating the apparatus of the invention shown in FIG. 2.

Referring now to FIG. 3, in a preferred embodiment of the invention, the apparatus 10 is positioned on a test hood 40, having a test chamber 42 disposed therein. As illustrated in FIG. 3, the hood 40 is provided with an entrance port 43 to facilitate placement of the infant's head 7 within the chamber 42.

As will be appreciated by one having ordinary skill in the art, the hood 40 may comprise various shapes and sizes, to position a patient's head (i.e., adult or infant) within a defined chamber or position the entire body of the infant 5 therein.

According to a preferred embodiment of the present invention, $\dot{V}CO$ and $\dot{V}H_2$ are determined in the following manner. The patient (i.e., infant 5) is positioned in test chamber 42.

Pump 18 is initiated and a "standard" of room air is drawn through line 32 at a selected flow rate, e.g., 50 ml/min, for a first period of time in the range of 30 to 75 sec. The "standard" is directed to and through the $CO_2$ and $CO/H_2$ detectors 12, 20.

At the end of a first time period, the sensed concentration of carbon dioxide ($CO'_2$), carbon monoxide ($CO'$) and hydrogen ($H'_2$) in the standard are obtained. A first signal from the $CO_2$ detector 12 corresponding to the sensed concentration $CO'_2$, and third and fourth signals from the $CO/H_2$ detector 20 corresponding to the concentrations of $CO'$ and $H'_2$, respectively, are communicated to the microprocessor 22 and stored in memory.

The microprocessor 22 then signals the regulator 16 to close line 32 and draw a test sample (i.e., analyte stream) from the chamber 42. The analyte stream is then directed to and through the filters 15, 14, and $CO_2$ and $CO/H_2$ detectors 12, 20.

During a second period of time (i.e., $t_1-t_0$), the sensed concentrations of carbon dioxide, carbon monoxide and hydrogen in the analyte stream, $CO_2''$, $CO''$ and $H_2''$, respectively, are obtained. In a preferred embodiment of the invention, the second period of time ($t_1-t_0$) is in the range of 60 to 120 sec.

A second signal corresponding to $CO_2''$ and the plurality of first and second signals $C_1-C_N$, $C'_1-C'_N$, corresponding to values of $CO''$ and $H_2''$ obtained over time period $t_1$ through $t_0$, are communicated to the microprocessor 22.

The noted values of $CO_2'$, $CO_2''$, $CO'$, $H_2'$, $C_1-C_N$, and $C'_1-C'_N$ are evaluated as follows: First, the values of the $CO_2$, $CO$ and $H_2$ obtained from the standard, i.e., $CO'_2$, $CO'$, $H'_2$, are compared to the values of the $CO_2$, $CO$ and $H_2$ obtained from the analyte stream, i.e., $CO_2''$, $CO''$, $H_2''$. The values $CO_2''$, $CO''$, $H_2''$ are then adjusted, if necessary, to account for the $CO_2'$, $CO'$ and $H_2'$ detected in the standard.

The values $\overset{\circ}{V}CO$ and $\overset{\circ}{V}H_2$ are then determined from the following relationships:

$$\overset{\circ}{V}CO = \int_{t_1}^{t_0} CO''_c dt \quad (1)$$

and $$\overset{\circ}{V}H_2 = \int_{t_1}^{t_0} H''_{2c} dt \quad (2)$$

where:

$t_1-t_0$=desired analyte stream test cycle or time interval;
$CO''_c$=corrected $CO''$ value; and
$H_2''_c$=corrected $H''$ value.

As will be appreciated by one having ordinary skill in the art, the method and apparatus of the invention provides several distinct advantages over the prior art. In contrast to the noted prior art methods that merely measure the concentration of CO in the end-tidal breath, which is not truly indicative of the physiological state of the patient, the method of the present invention provides rapid, accurate, direct in vivo measurement of $VCO$ and $VH_2$.

A further advantage is that the apparatus is compact, lightweight and readily adaptable to virtually all-testing environments.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An apparatus for in vivo measurement of carbon monoxide production rate in a subject comprising:
   a first gas detector for detecting the concentration of a first selected gas in at least a first and second gas sample, said first gas detector being adapted to provide at least a first output signal indicative of said first selected gas concentration in said first gas sample and a second output signal indicative of said first selected gas concentration in said second gas sample;
   a second gas detector in communication with said first gas detector, said second gas detector being adapted to substantially simultaneously detect the concentration of at least a second and third selected gas in at least said first and second gas samples, said second gas detector being further adapted to provide at least a third output signal indicative of said second selected gas concentration in said first gas sample, a fourth output signal indicative of said second selected gas concentration in said second gas sample, a fifth output signal indicative of said third selected gas concentration in said second gas sample and a sixth output signal indicative of said third selected gas concentration in said second gas sample;
   means for providing said first and second gas samples to said first and second gas detectors; and
   processing means in communication with said first and second gas detectors for determining the rate of carbon monoxide production in at least said second sample in response to said first, second, third, fourth, fifth and sixth output signals.

2. The apparatus of claim 1, wherein said first selected gas comprises carbon dioxide.

3. The apparatus of claim 1, wherein said second selected gas comprises carbon monoxide.

4. The apparatus of claim 1, wherein said third selected gas comprises hydrogen.

5. The apparatus of claim 1, wherein said first gas sample substantially comprises room air.

6. The apparatus of claim 1, wherein said second gas sample comprises an expired breath sample from said subject.

7. The apparatus of claim 1, wherein said means for providing said first and second gas samples includes a flow regulator and flow inducing means.

8. The apparatus of claim 7, wherein said flow inducing means comprises a positive displacement pump.

9. The apparatus of claim 1, wherein said apparatus includes an organic vapor filter disposed between said first and second gas detectors.

10. The apparatus of claim 9, wherein said organic vapor filter substantially comprises activated charcoal.

11. A method for measuring the carbon monoxide production rate of a subject, comprising the steps of:
    introducing a room air sample to first and second gas detectors during a first period of time;
    detecting the concentration of carbon dioxide in said room air sample ($CO_2$) with said first gas detector during said first period of time;

substantially simultaneously detecting the concentration of carbon monoxide in said room air sample (CO) and the concentration of hydrogen in said ambient room air sample ($H_2$) with said second gas detector during said first period of time;

introducing a breath sample from said subject to said first and second gas detectors during a second period of time;

measuring the concentration of carbon dioxide in said breath sample ($CO_2'$) with said first gas detector during said second period of time;

substantially simultaneously measuring the concentration of carbon monoxide in said breath sample (CO') and the concentration of hydrogen in said breath sample ($H_2'$) with said second gas detector during said second period of time;

comparing said $CO_2'$, CO', and $H_2'$ detected in said breath sample to said $CO_2$, CO and $H_2$ detected in said room air sample to derive corrected carbon dioxide ($CO_2''$), carbon monoxide (CO'') and hydrogen ($H_2''$) values; and determining the carbon monoxide production rate ($\dot{V}CO$) from the following relationship:

$$\overset{\circ}{V}CO = \int_{t_1}^{t_o} CO'' dt$$

where:

$t_1 - t_0$ = said second period of time.

12. The method of claim 11, wherein said method includes the step of determining the hydrogen production rate ($\dot{V}H_2$) from the following relationship:

$$\overset{\circ}{V}H_2 = \int_{t_1}^{t_o} H_2'' dt$$

13. The method of claim 11, wherein said first period of time is in the range of approximately 30 to 75 sec.

14. The method claim 11, wherein said second period of time is in the range of approximately 60 to 120 sec.

* * * * *